(12) United States Patent
Biedermann et al.

(10) Patent No.: US 9,192,413 B2
(45) Date of Patent: Nov. 24, 2015

(54) POLYAXIAL BONE ANCHORING DEVICE

(75) Inventors: Lutz Biedermann, VS-Villingen (DE); Gerhard Pohl, St. Georgen (DE)

(73) Assignee: Biedermann Technologies GmbH & Co. KG, Donaeuschingen (DE)

( * ) Notice: Subject to any disclaimer, the term of this patent is extended or adjusted under 35 U.S.C. 154(b) by 510 days.

(21) Appl. No.: 13/303,111

(22) Filed: Nov. 22, 2011

(65) Prior Publication Data

US 2012/0143265 A1 Jun. 7, 2012

Related U.S. Application Data

(60) Provisional application No. 61/416,137, filed on Nov. 22, 2010, provisional application No. 61/449,349, filed on Mar. 4, 2011.

(30) Foreign Application Priority Data

Nov. 22, 2010 (EP) .................................... 10192079

(51) Int. Cl.
*A61B 17/84* (2006.01)
*A61B 17/70* (2006.01)
*A61B 17/00* (2006.01)

(52) U.S. Cl.
CPC .......... *A61B 17/7035* (2013.01); *A61B 17/7032* (2013.01); *A61B 2017/00526* (2013.01)

(58) Field of Classification Search
CPC . A61B 17/84; A61B 17/7035; A61B 17/7032
USPC ............................. 606/60, 246–279, 300–331
See application file for complete search history.

(56) References Cited

U.S. PATENT DOCUMENTS

| | | | |
|---|---|---|---|
| 5,558,674 A | 9/1996 | Heggeness et al. | |
| 5,672,176 A | 9/1997 | Biedermann et al. | |
| 5,681,319 A * | 10/1997 | Biedermann et al. | ......... 606/104 |
| 5,716,356 A | 2/1998 | Biedermann et al. | |

(Continued)

FOREIGN PATENT DOCUMENTS

| | | |
|---|---|---|
| FR | 2 684 866 A1 | 6/1993 |
| JP | 2003-204971 A | 7/2003 |

(Continued)

OTHER PUBLICATIONS

European Search Report for European Application No. 10 19 2079.1, European Search Report dated Mar. 11, 2011 (6 pgs.).

*Primary Examiner* — Christopher Beccia
(74) *Attorney, Agent, or Firm* — Christie, Parker & Hale, LLP

(57) ABSTRACT

A polyaxial bone anchoring device includes an anchoring element having a shaft and a head, a receiving part having a seat for receiving the head, a pressure element to exert pressure onto the head, wherein the head is pivotable and can be locked at an angle relative to the receiving part, wherein an outer wall of the pressure element has a recess or a deformable portion, and an inner wall of the receiving part has a deformable portion or a recess, wherein the pressure element is movable from a first position wherein the deformable portion protrudes a first distance into the recess while the head is pivotable relative to the receiving part, to a second position wherein the deformable portion protrudes a second distance into the recess, such that a force holds the head at one of a plurality of releasable angular positions before locking the head.

26 Claims, 10 Drawing Sheets

(56) References Cited

U.S. PATENT DOCUMENTS

| | | |
|---|---|---|
| 7,087,057 B2 | 8/2006 | Konieczynski et al. |
| 7,311,712 B2 * | 12/2007 | Dalton .......................... 606/71 |
| 7,604,656 B2 | 10/2009 | Shluzas |
| 8,137,386 B2 * | 3/2012 | Jackson ....................... 606/266 |
| 2003/0125741 A1 | 7/2003 | Biedermann et al. |
| 2004/0267264 A1 | 12/2004 | Konieczynski et al. |
| 2005/0049589 A1 | 3/2005 | Jackson |
| 2006/0264933 A1 | 11/2006 | Baker et al. |
| 2008/0045953 A1 * | 2/2008 | Garamszegi .................... 606/61 |
| 2009/0062867 A1 * | 3/2009 | Schumacher ................. 606/308 |
| 2010/0137920 A1 | 6/2010 | Hammill, Sr. et al. |
| 2010/0160977 A1 | 6/2010 | Gephart et al. |
| 2010/0234902 A1 | 9/2010 | Biedermann et al. |

FOREIGN PATENT DOCUMENTS

| | | |
|---|---|---|
| JP | 2007-526007 A | 9/2007 |
| JP | 2010-194309 A | 9/2010 |
| JP | 2010-534116 A | 11/2010 |
| WO | WO 2005/004699 A2 | 1/2005 |
| WO | WO 2009/015100 A2 | 1/2009 |
| WO | WO 2010/103198 A1 | 9/2010 |

* cited by examiner

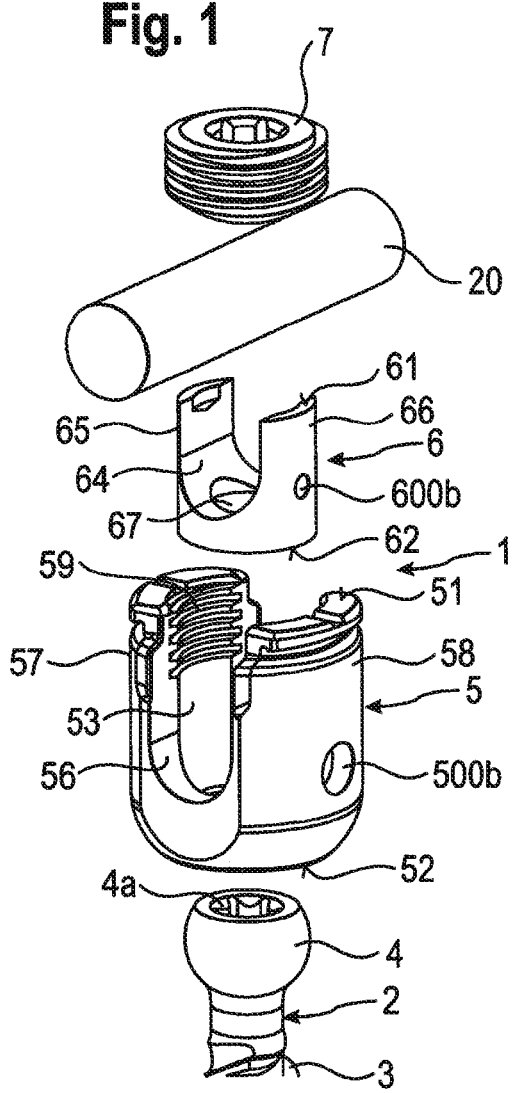
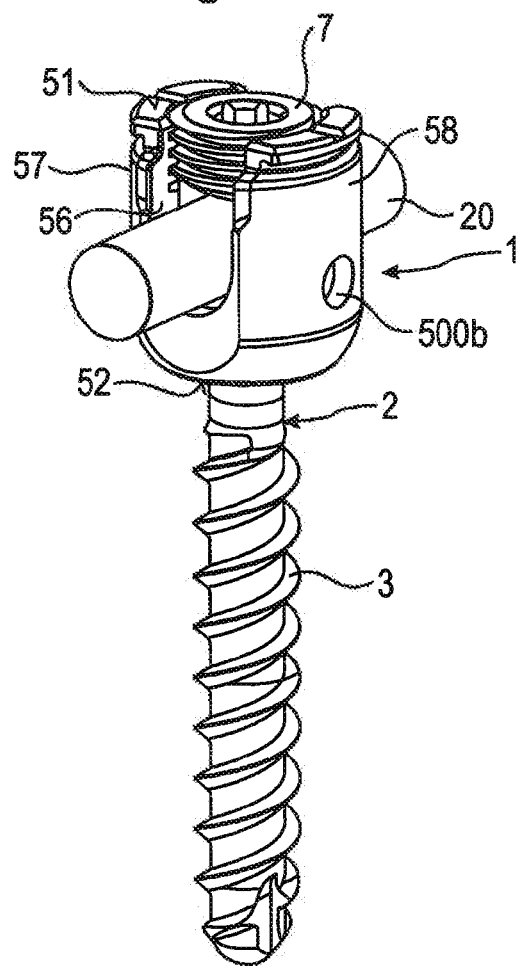

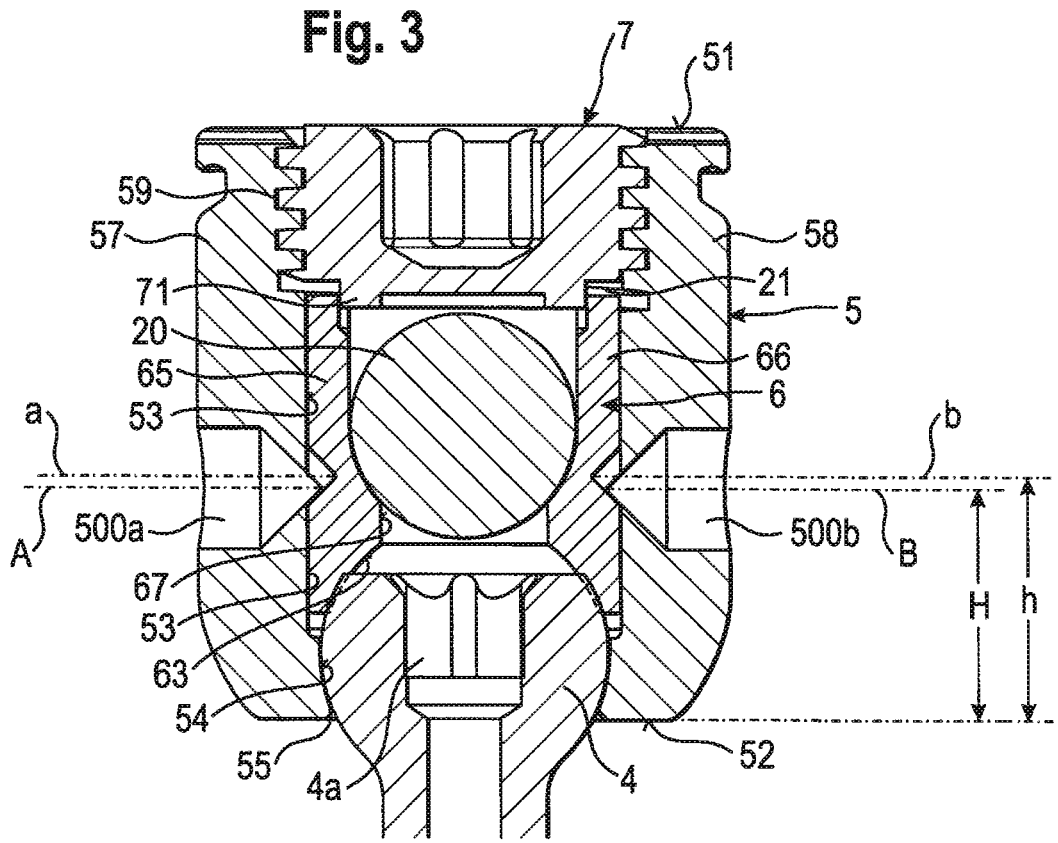

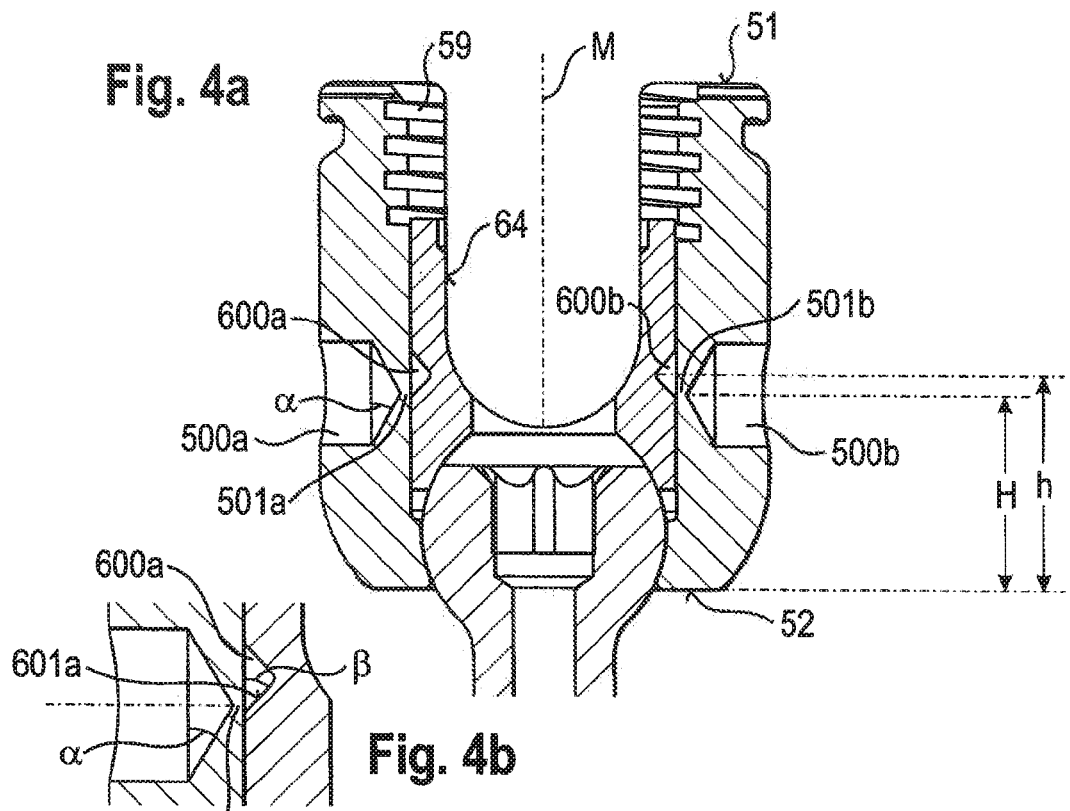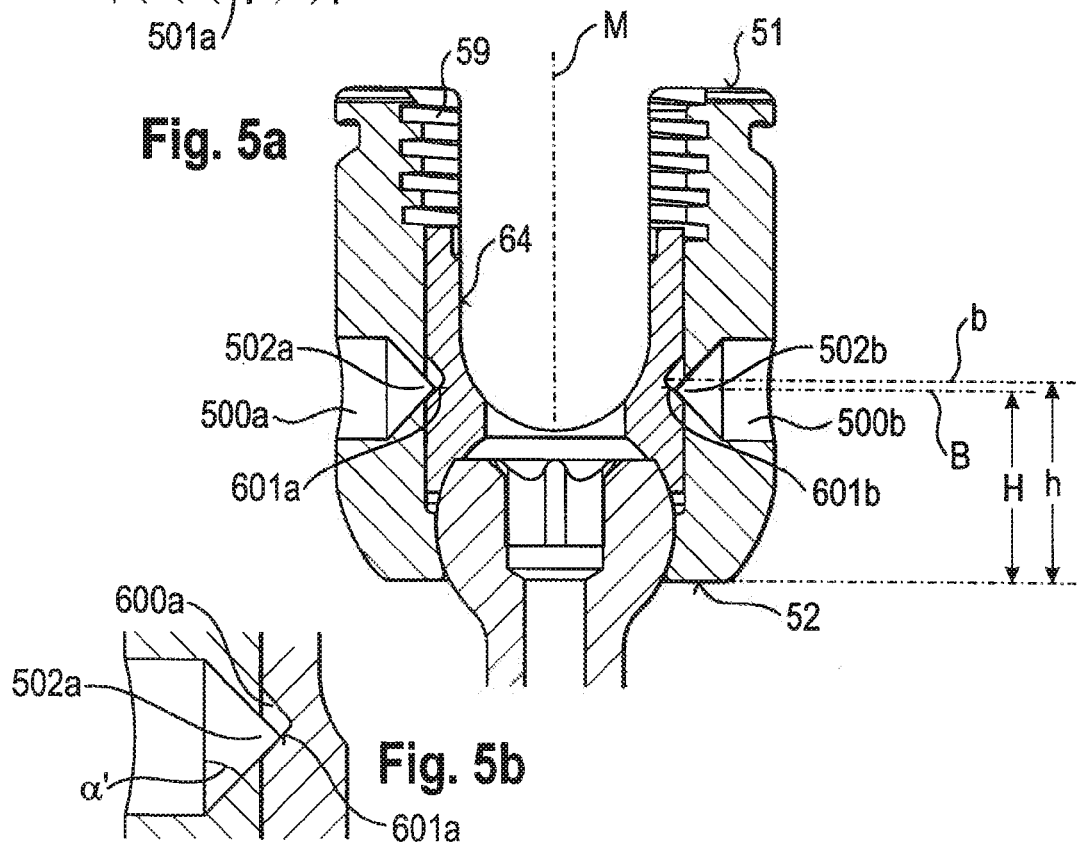

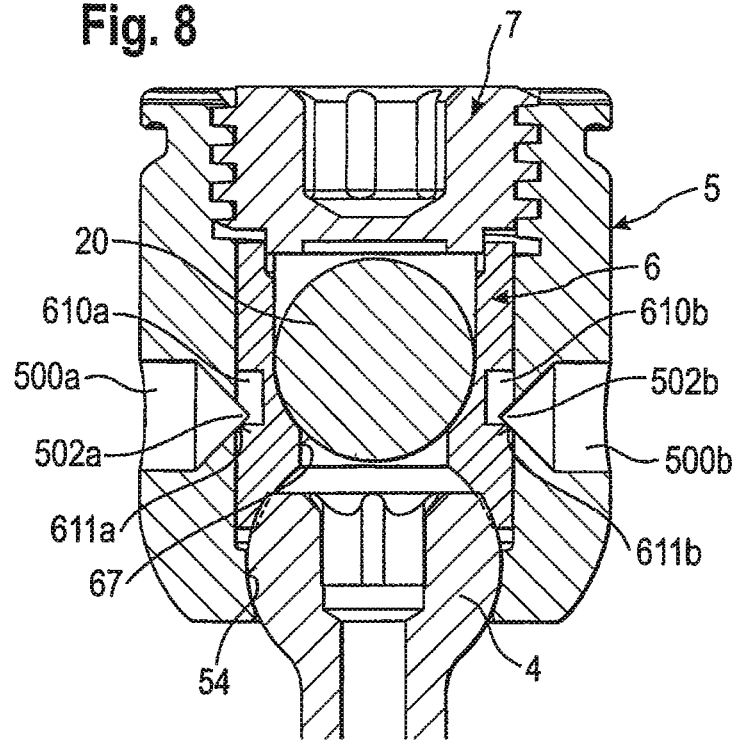
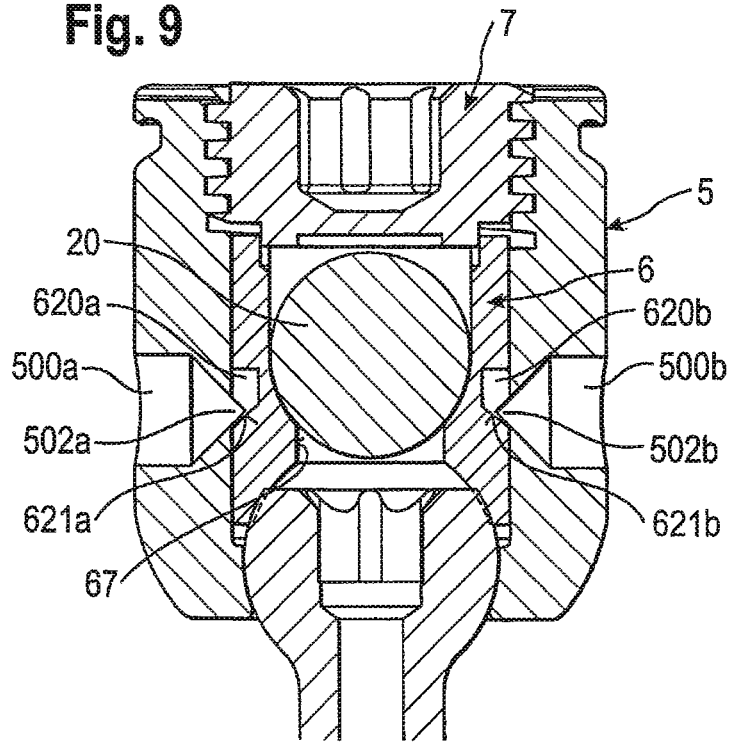

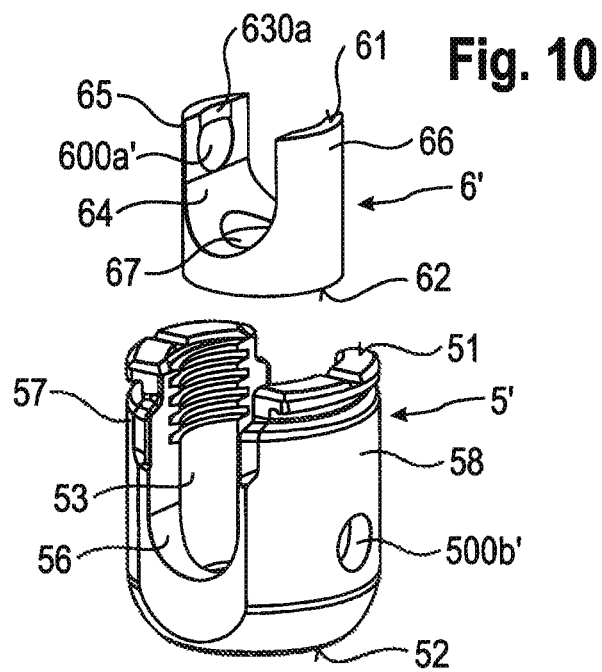
Fig. 10
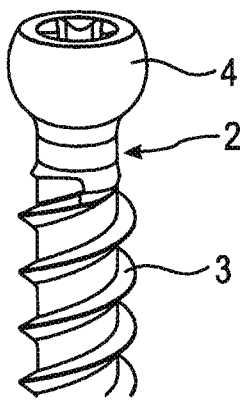
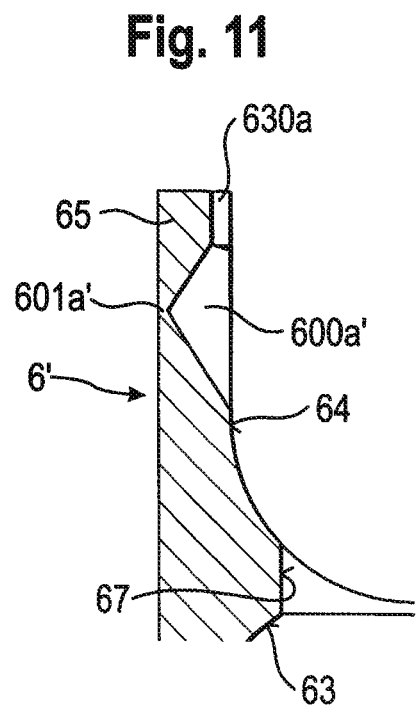
Fig. 11

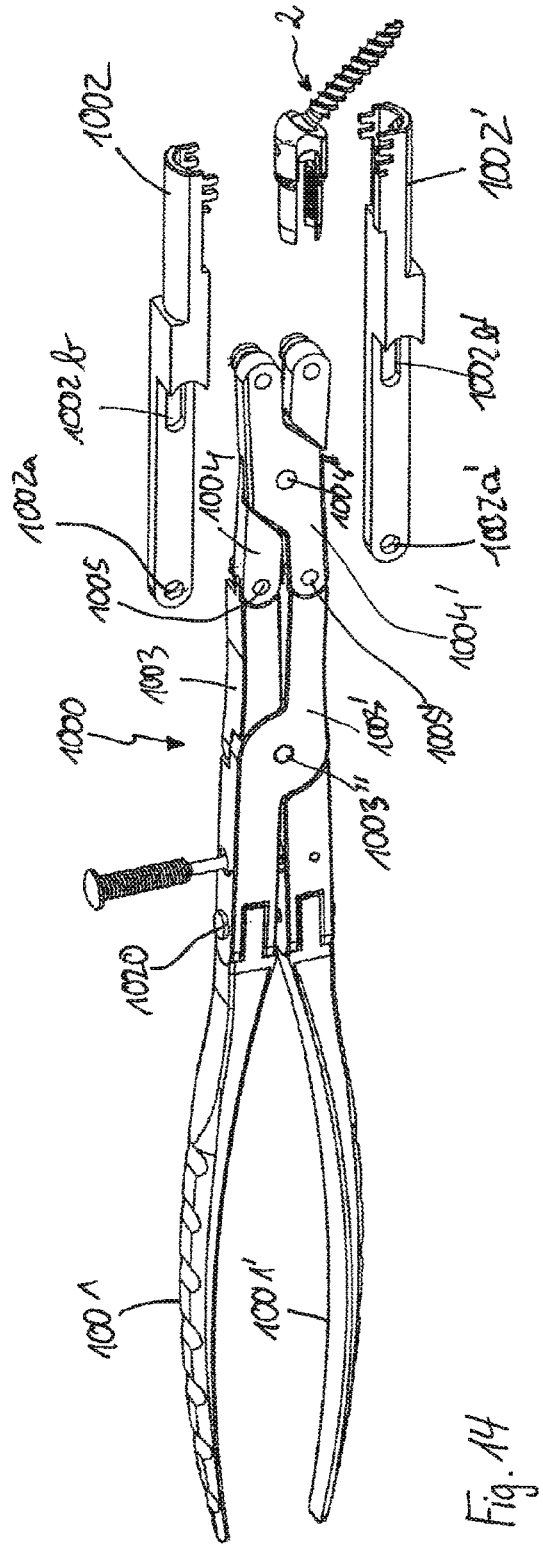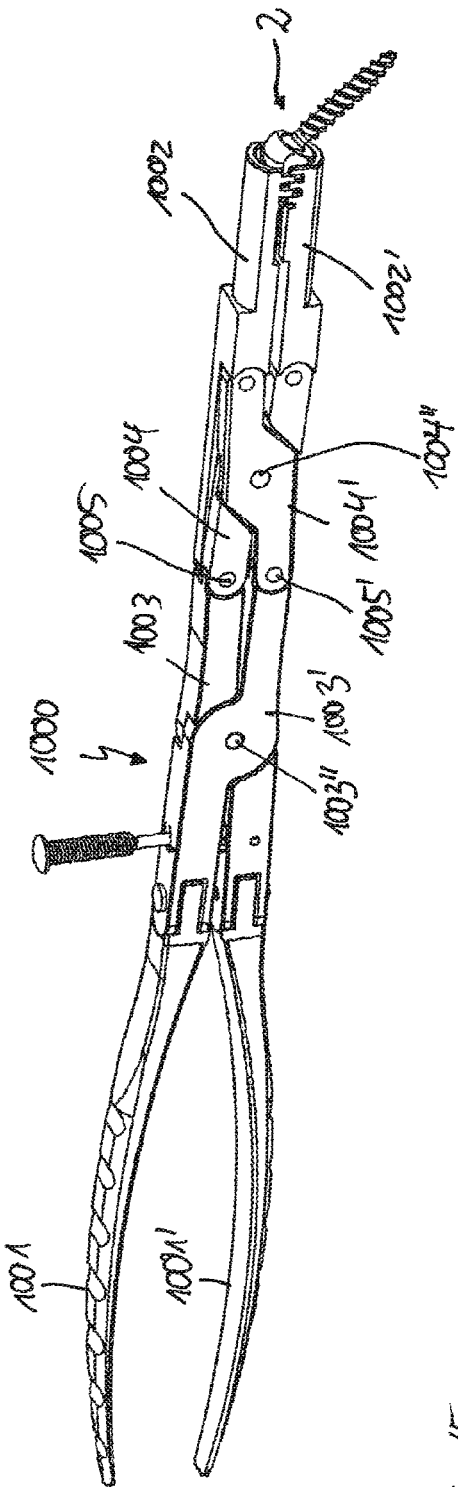

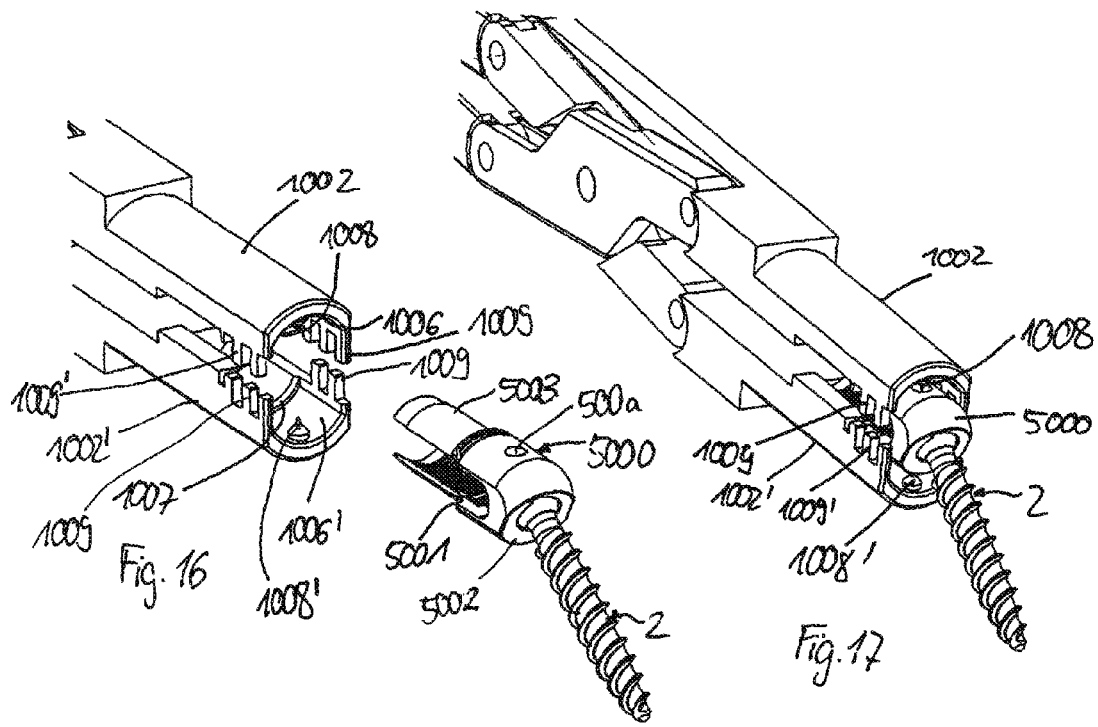
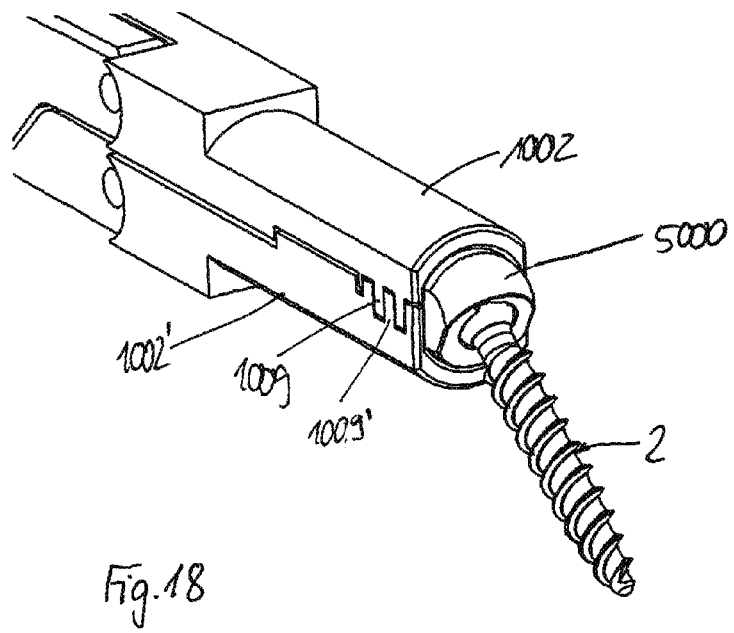

POLYAXIAL BONE ANCHORING DEVICE

CROSS REFERENCE TO RELATED APPLICATIONS

The present application claims the benefit of U.S. Provisional Patent Application Ser. No. 61/416,137, filed Nov. 22, 2010, and No. 61/449,349, filed Mar. 4, 2011, the contents of which are hereby incorporated by reference in their entirety, and claims priority to European Patent Application No. EP 10 192 079.1, filed Nov. 22, 2010, the contents of which are hereby incorporated by reference in their entirety.

BACKGROUND

1. Field of the Invention

The invention relates to a polyaxial bone anchoring device for anchoring a stabilization rod in a bone or in a vertebra. The bone anchoring device includes an anchoring element, a receiving part for receiving a head of the bone anchoring element and for receiving a stabilization rod to be connected to the bone anchoring element. The bone anchoring element is pivotably connected to the receiving part and can be locked at an angle by exerting pressure onto a head of the bone anchoring element via a pressure element that is arranged in the receiving part. The pressure element and the receiving part are configured to cooperate in such a way that the pressure element frictionally clamps the head to maintain a desired angular position before finally locking the angular position.

2. Description of Related Art

U.S. Pat. No. 5,716,356 describes a polyaxial bone screw including a screw element and a receiving part which is pivotably connected to the screw element and a pressure element to exert pressure onto the head of the screw element to lock the angle between the screw element and the receiving part. The receiving part has a U-shaped channel for receiving a stabilization rod. The pressure element comprises a cylindrical recess, which is to be aligned with the U-shaped channel to receive the rod therein. In order to hold the pressure element in a position aligned with the U-shaped channel, the position of the pressure element is fixed by crimping through bores provided in the receiving part.

When the head of the bone anchoring element is freely pivotable with respect to the receiving part before locking the head in a final angular position, the alignment of the receiving part and the insertion of the rod may be difficult in more complex clinical applications, for example, when a multitude of bone anchors have to be connected to the rod.

U.S. Pat. No. 7,604,656 describes a fastener engageable with a bone portion to connect a longitudinal member to the bone portion. The housing that receives the fastener also receives a spacer, which is engageable with the fastener and the longitudinal member. In one embodiment, the spacer is urged by a pin member into frictional engagement with the fastener and with the housing.

US 2004/0267264 A1 describes a polyaxial fixation device, wherein the polyaxial bone screw includes an engagement member that is adapted to provide sufficient friction between the spherical head and the receiver member to enable the shank to be maintained in a desired angular orientation before locking the spherical head within the receiver member. The engagement member is realized, for example, by a snap ring around the head or by spring members provided at the compression cap to frictionally engage the spherical head or by a slot provided in the compression cap.

SUMMARY

It is an object of the invention to provide a polyaxial bone anchoring device and a method for manufacturing the same, which allows for improved handling during surgery and which can be manufactured in a simple manner.

With a polyaxial bone anchoring device according to embodiments of the invention, a temporary clamping of a head of a bone anchoring element in a desired angular position with respect to a receiving part, without finally locking the head, can be achieved. This allows for maintaining the receiving part in an adjustable angular position relative to the bone anchoring element. In this condition, a pressure element exerts a preload onto the head, such that the head is not locked, but is prevented from freely pivoting. When the head is temporarily clamped, the alignment of the receiving part with respect to the rod and the insertion of the rod is more readily facilitated, in particular, in a situation in which a multitude of bone anchoring devices have to be connected to the rod.

When the rod is inserted into the receiving part, adjustments of the rod is still possible without completely loosening the head.

The polyaxial bone anchoring device according to embodiments of the invention includes few parts which are of simple design. A mechanism to frictionally clamp the head before finally locking the head is free from or does not include any spring members or portions. This facilitates easier manufacturing of the polyaxial bone anchoring device. Furthermore, existing receiving parts and pressure elements can be used without having to redesign their shape. It is possible to simply change a location of crimp bores described in the following embodiments.

An amount of preload exerted onto the head by the pressure element can be exactly or accurately predefined in a simple manner by selecting a position and shape of the crimp bores. A polyaxial bone anchoring device according to exemplary embodiments may be provided to a surgeon or practitioner in a pre-assembled manner, in which the pressure element is axially and rotationally fixed to such an extent that it cannot fall out or be rotated out of its aligned position in the receiving part. This allows for safer handling by the surgeon or practitioner.

The receiving part and the pressure element can be manufactured in series at low costs.

BRIEF DESCRIPTION OF THE DRAWINGS

Further features and advantages of the invention will become apparent from the description of embodiments by means of the accompanying drawings. In the drawings:

FIG. 1 shows a perspective exploded view of a polyaxial bone anchoring device according to a first embodiment;

FIG. 2 shows the polyaxial bone anchoring device of FIG. 1 in an assembled state;

FIG. 3 shows a cross-sectional view of the polyaxial bone anchoring device of FIG. 1 in an assembled state before final locking of a head of a bone anchoring element in a receiving part;

FIG. 4a shows a cross-sectional view of the polyaxial bone anchoring device of FIG. 1 before provisionally fixing a pressure element in the receiving part;

FIG. 4b shows an enlarged portion of FIG. 4a;

FIG. 5a shows a cross-sectional view of the polyaxial bone anchoring device of FIG. 1 in the pre-assembled state after provisionally fixing of the pressure element in the receiving part;

FIG. 5b shows an enlarged portion of FIG. 5a;

FIG. 8 shows a cross-sectional view of a modified embodiment of a polyaxial bone anchoring device before locking of a head of a bone anchoring element in a receiving part;

FIG. 9 shows a cross-sectional view of a further modified embodiment of a polyaxial bone anchoring device in a state before locking of a head of a bone anchoring element in a receiving part;

FIG. 10 shows a perspective exploded view of a second embodiment of a polyaxial bone anchoring device;

FIG. 11 shows an enlarged cross-sectional view of a portion of a pressure element of the bone anchoring device of FIG. 10;

FIG. 14 shows a perspective exploded view of a further crimping tool according to another exemplary embodiment that can be hand-operated;

FIG. 15 shows a perspective view of the crimping tool of FIG. 14 in an assembled state;

FIG. 16 shows an enlarged perspective view of a portion of the crimping tool of FIGS. 14 and 15 with claws in an opened state and with a polyaxial bone anchoring device not yet inserted into the tool;

FIG. 17 shows an enlarged perspective view of a portion of the crimping tool of FIGS. 14 and 15 with the polyaxial bone anchoring device inserted and the claws not yet fully closed;

FIG. 18 shows an enlarged perspective view of a portion of the crimping tool of FIGS. 14 and 15 with the polyaxial bone anchoring device inserted and the claws closed;

FIG. 19a shows a cross-sectional view of a portion of the crimping tool of FIGS. 14 and 15 with the polyaxial bone anchoring device inserted and the claws not yet closed, the section being taken perpendicular to a rod axis of the polyaxial bone anchoring device;

FIG. 19b shows an enlarged cross-sectional view of a portion of FIG. 19a;

FIG. 20a shows a cross-sectional view of a portion of the crimping tool of FIGS. 14 and 15 with the polyaxial bone anchoring device inserted and the claws closed, the section being taken perpendicular to the rod axis of the polyaxial bone anchoring device; and FIG. 20b shows an enlarged cross-sectional view of a portion of FIG. 20a.

DETAILED DESCRIPTION

Figure 6:
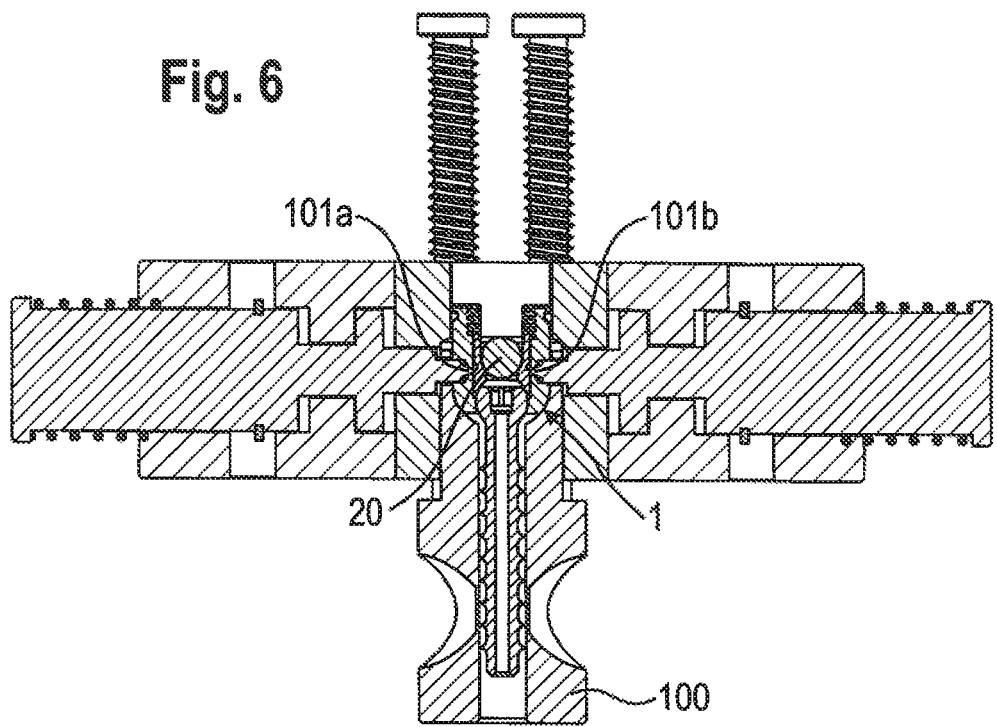
FIG. 6 shows a cross-sectional view of a tool according to an exemplary embodiment for provisionally fixing the pressure element in the receiving part.
Figure 7:
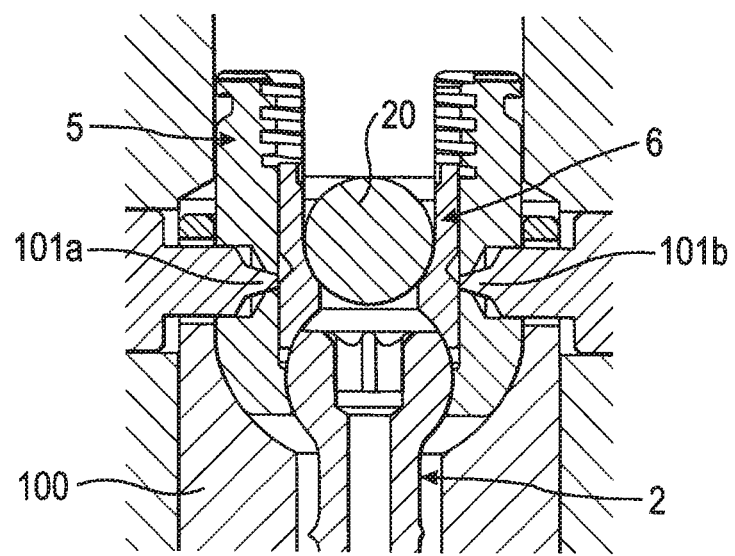
FIG. 7 shows an enlarged portion of FIG. 6.

A polyaxial bone anchoring device 1 according to a first embodiment as shown in FIGS. 1 to 3 includes a bone anchoring element in the form of a screw member 2 having a threaded shaft 3 and a head 4. The head 4 is generally spherical and includes a recess 4a at a free end for engagement with a tool to insert the threaded shaft 3 into bone. The bone anchoring device further includes a receiving part 5 for connecting the screw member 2 to a rod 20. A pressure element 6 can be arranged in the receiving part on top of the head 4. In addition, for securing the rod 20 in the receiving part 5 and for exerting pressure onto the head 4, a locking device, for example, an inner screw 7, which cooperates with the receiving part 5, is provided.

The receiving part 5 is a substantially cylindrical one piece part and has a top end 51 and a bottom end 52. A passageway extending from the top end 51 to the bottom end 52 is formed by a coaxial bore 53 followed by a seat portion 54 for receiving the head 4 of the screw member 2. The seat portion 54 has an opening 55 at the bottom end 52 through which the shaft 3 of the screw member 2 can extend. The seat portion 54 is shown to be spherically-shaped, but can alternatively be tapered or can have any other shape that allows for receiving of the head 4, so that the head 4 can pivot with respect to the receiving part 5. At the top end 51a substantially U-shaped recess 56 is provided by means of which two free legs 57, 58 are formed which serve as sidewalls of a channel for receiving the rod 20. An internal thread 59 is provided at the legs 57, 58 for cooperating with the inner screw 7.

The pressure element 6 may be formed in one piece. The pressure element 6 is of substantially cylindrical construction and has an outer diameter which allows it to move in an axial direction within the bore 53 of the receiving part 5. The pressure element 6 has a top end 61 and a bottom end 62. When the pressure element 6 is inserted into the receiving part 5, the bottom end 62 faces the head 4 of an inserted screw element 2. At the bottom end 62, a spherical recess 63 is provided, which may be adapted to the size and shape of the head 4. The spherical recess 63 is configured to come into frictional engagement with the spherical surface of the head 4. At the top end 61, a U-shaped recess 64 is provided by means of which two free legs 65, 66 are formed to form a channel to receive the rod 20 therein. Furthermore, the pressure element 6 includes a coaxial bore 67 for accessing the screw head 4 with a tool (not shown) while the head 4 and the pressure element 6 are in the receiving part 5. As shown in the figures, the pressure element 6 may be a solid member without any spring portions which could render it more flexible. The pressure element 6 is arranged in the receiving part 5 such that the U-shaped recess 56 of the receiving part 5 and the U-shaped recess 64 of the pressure element 6 are aligned.

In an assembled state as shown in FIG. 3, the screw head 4 is located in the seat portion 54 and the pressure element 6 is arranged on top of the screw head 4. The height of the free legs 65, 66 of the pressure element 6 are configured such that the free legs 65, 66 extend above the rod 20 when the rod 20 is inserted and is resting on the bottom of the channel of the pressure element 6.

The locking device in the form of the inner screw 7 has a projection 71 extending into the channel formed by the free legs 65, 66 of the pressure element 6. The size of the projection 71 in an axial direction is such that when the inner screw 7 is tightened, the projection 71 presses onto the rod while there is still a gap 21 between the top end 61 of the pressure element 6 and a lower side of the inner screw 7. Therefore, with a single inner screw 7, pressure can be exerted onto the rod 20 only, where the rod 20 can in turn exert pressure onto the pressure element 6. It should be noted that instead of the single part locking device in the form of the inner screw 7, a two-part locking device can instead be used (not shown). Such a two-part locking device includes a first part to be screwed in between the legs 57, 58 of the receiving part 5. The first part acts onto the top end 61 of the pressure element 6. Further, a second part in the form of an inner screw is provided in the first part, where the second part presses onto the rod 20. By means of this, the head 4 and the rod 20 can be independently fixed relative to the receiving part 5.

The pressure element 6 is retained in the receiving part 5 as shown in FIGS. 3 to 5b. As shown in particular in FIGS. 4a and 4b, the receiving part 5 includes two blind holes 500a, 500b forming crimp bores that extend from an outer surface of the receiving part 5 to a distance from an inner wall of the coaxial bore 53. The blind holes 500a, 500b are arranged to be 180° offset from each other and at 90° with respect to a center of the channel formed by the U-shaped recess 56. The blind holes 500a, 500b are aligned perpendicular with respect to a bore axis M of the coaxial bore 53. At their ends, the blind holes 500a, 500b are tapered with an angle α that is preferably less than 45°, for example 22.5°, with respect to an axis parallel to the bore axis M. Bore axes A and B of the blind holes 500a, 500b are provided at a distance H from the second end 52 of the receiving part 5.

The portions of the receiving part 5 that are between the closed ends of the blind holes 500a, 500b and the coaxial bore 53 of the receiving part 5 are configured to be deformable portions 501a, 501b.

The pressure element 6 correspondingly includes two recesses 600a, 600b which are 180° offset from each other and 90° offset from a center of the channel formed by the U-shaped recess 64. The recesses 600a, 600b have center axes a, b, respectively, which are perpendicular to the bore axis M. In the embodiment shown, the recesses 600a, 600b have a conical shape. Downwardly extending flanks 601a, 601b of the recesses 600a, 600b each include an angle β of approximately 45° relative to the central bore axis M. As shown in FIGS. 4a and 4b, when the pressure element 6 is inserted such that it rests on the head 4 of the screw element 2, the central axes a, b of the recesses 600a, 600b may be a distance h from the second end 52 of the receiving part 5 that is greater than the distance H of the central axes A, B of the blind holes 500a, 500b. In other words, the recesses 600a, 600b may be arranged or positioned above the blind holes 500a, 500b.

The distance between the recesses 600a, 600b and the blind holes 500a, 500b is such that when the deformable portions 501a, 501b are deformed by applying a force via, for example, a crimping tool inserted in the blind holes 500a, 500b, the deformed material protrudes from the inner wall of the receiving part 5 and may press onto the lower flanks 601a, 601b of the recesses 600a, 600b, respectively, to exert a downward force onto the pressure element 6. As shown in FIGS. 5a and 5b, deforming the deformable portions 501a, 501b may result in or form deformed portions 502a, 502b, which exert pressure on the lower flank 601a, 601b of the recesses 600a, 600b of the pressure element 6. For example, after deformation, the angle α may be increased to be approximately 45°, which is approximately the same as the angle β of the lower flank 601a, 601b. The blind holes 500a, 500b with their respective deformable portions 501a, 501b and the recesses 600a, 600b are constructed such that by deforming the deformable portions 501a, 501b into deformed portions 502a, 502b which engage the recesses 600a, 600b, the resulting force onto the pressure element 6 generates a preload onto the head 4, due to, for example, the positioning of the pressure element 6 which clamps the head 4 by means of friction. By selecting the sizes of the blind holes 500a, 500b and the recesses 600a, 600b and their positions, a desired friction force can be achieved. By this friction force, the head 4 can be maintained in a desired angular position and can be moved out of this position by applying a force greater than the friction force either to the screw element 2 or to the receiving part 5. Simultaneously, the pressure element 6 is secured against rotation and secured against escaping through the top end 51 of the receiving part 5. The recesses 600a, 600b provide space for accommodating a part of the deformed material. Also, the recesses 600a, 600b provide space for the protrusions 502a, 502b when the pressure element 6 moves downward (e.g., towards the second end 52) to finally lock the head 4.

A method for manufacturing a polyaxial bone anchoring device according to an embodiment of the invention is explained with reference to FIGS. 4a to 7. A crimping tool shown in FIGS. 6 and 7 generally includes a holder 100 for a bone anchoring device 1, which serves for fixing a receiving part 5 with an inserted screw element 2 and pressure element 6, as shown in FIGS. 4a and 4b. A rod 20 may be inserted for providing a counter-force to avoid deformation of free legs 65, 66 of the pressure element 6. The crimping tool further includes two crimping tips 101a, 101b, which are arranged 180° offset from each other and are dimensioned to be introduced into blind holes 500a, 500b and to deform deformable portions 501a, 501b, so that the displaced or deformed material, which forms deformed portions 502a, 502b, engage recesses 600a, 600b of the pressure element 6. As can be seen in particular in FIG. 7, the crimping tips 101a, 101b have an angle which is more acute than that of the bottom of the blind holes 500a, 500b. The crimping tips 101a, 101b deform the deformable portions 501a, 501b, such that the deformed portions 502a, 502b, can press onto lower flanks 601a, 601b of the recesses 600a, 600b, respectively. Thereafter, the crimping tips 101a, 101b are retracted. The crimping process can be force-actuated and/or path-controlled.

After the crimping tips 101a, 101b are retracted, the polyaxial anchoring device 1 can be removed from the holder 100. The polyaxial bone anchoring device is then in a pre-assembled state with the screw element 2 being inserted and the pressure element 6 being held in such a way that the pressure element 6 exerts a slight preload onto the head 4, which frictionally holds the head 4 in a temporary angular position.

It shall be noted that the shape of the blind holes may vary. In particular, the angle of the conical bottom may vary or the bottom may have a rounded or other shape. The recesses provided at the pressure element 6 may also have a different shape. For example, as shown in FIG. 8, recesses 610a, 610b can have, for example, a substantially rectangular cross-section. A lower side of the recesses 610a, 610b may have an inclined edge 611a, 611b for engagement with the deformed portions 502a, 502b.

In another modified embodiment, as shown in FIG. 9, a cross-section of recesses 620a, 620b of the pressure element 6 can be, for example, trapezoidal, with an inclined lower flank 621a, 621b for engagement with the deformed portions 502a, 502b.

All parts of the bone anchoring device may be made of a body-compatible material, such as a body-compatible metal, for example, titanium, of body-compatible metal alloys such as, for example, Nitinol, or of a body-compatible plastic material, such as, for example, polyether ether ketone (PEEK), or various combinations thereof.

Usually, several bone anchoring devices are utilized for stabilizing bone parts or vertebrae with a rod. In use, the bone anchoring devices may be pre-assembled as shown in FIGS. 5a and 5b. The screw members 2 are screwed into respective bone or vertebra. Then, the receiving parts 5 are pivoted by applying a force greater than a preload friction force, until each receiving part 5 has a correct or desired orientation for the insertion of a rod 20. Due to the friction force, each receiving part 5 is held in its respective temporary angular position. Thereafter, the rod 20, which connects the bone anchoring devices, is inserted and the inner screws 7 are tightened to move respective pressure elements 6 downwards to lock the heads 4 in the respective seats 54, so that the angular positions of the screw members 2 with respect to the receiving parts 5 are fixed. The rod 20 is simultaneously fixed by the inner screws 7. Since the deformed portions 502a, 502b engage only the lower flank 601a, 601b of the recesses 600a, 600b provided at the pressure elements 6, the recesses 600a, 600b provide enough space for the deformed portions 502a, 502b to allow for a downward movement of the pressure elements 6 relative to their respective receiving parts 5.

Further modifications of the previously described embodiment are conceivable. For example, only one deformed portion at the receiving part and one corresponding recess at the pressure element may be sufficient. In other embodiments, more than two deformed portions and corresponding recesses can also be provided.

A second embodiment of the bone anchoring device is described with reference to FIGS. 10 to 13. Parts or portions that are identical or similar to the previously described embodiments are designated with the same reference numerals, and the descriptions thereof will not be repeated. The second embodiment differs from the first embodiment mainly in that the functions of the pressure element and the receiving part, with respect to the provisional fixation by imparting a preload onto the head of the bone anchoring element, are reversed.

Figure 12:
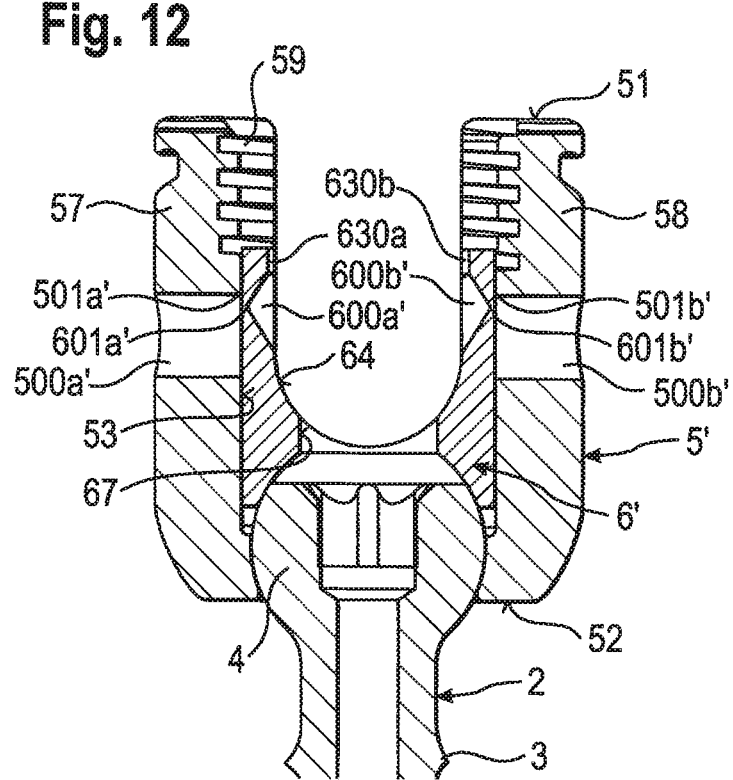
FIG. 12 shows a cross-sectional view of the polyaxial bone anchoring device of the second embodiment before provisionally fixing the pressure element in a receiving part.
Figure 13:
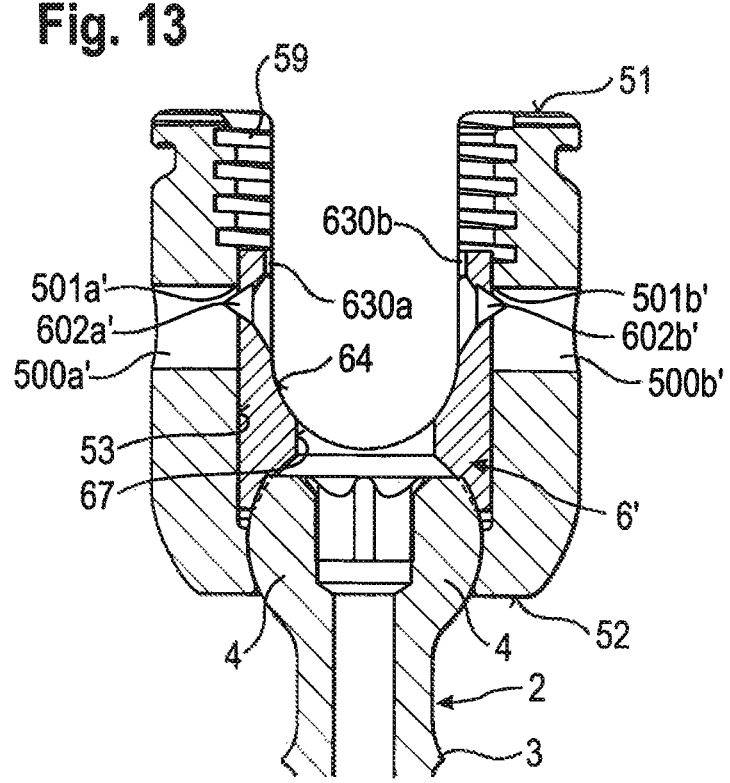
FIG. 13 shows a cross-sectional view of the polyaxial bone anchoring device of FIG. 12 in a pre-assembled state after provisionally fixing the pressure element in the receiving part.

As can be seen in FIGS. 10 and 12-13, the receiving part 5' has, instead of blind holes 500a, 500b, two through holes 500a', 500b'. In some embodiments, recesses at an inner wall of the receiving part 5' instead of through holes 500a', 500b' may be sufficient. However, through holes are generally easier to manufacture and allow for easier upgrading or modification of existing receiving parts that already have blind holes as seen in the first embodiment.

The pressure element 6' has two recesses 600a', 600W, arranged to be offset by 180°, that extend from an inner wall of channel 64 into legs 65, 66, respectively. The recesses 600a', 600b' may each have a substantially triangular cross-section with a taper of approximately 22.5° similar to that of the blind holes 500a, 500b of the receiving part 5 of the first embodiment. At an upper edge of the recesses 600a', 600b', rectangular recesses 630a, 630b may be provided, respectively, the depths of which are less than that of the recesses 600a', 600b'. The recesses 630a, 630b are optional and may help facilitate the insertion of a crimping tool.

Between an outer surface of the pressure element 6' and bottoms of the recesses 600a', 600b', deformable portions 601a', 601b' can be deformed into deformed portions 602a', 602b', as shown, for example, in FIG. 13. In the pre-assembled and non-deformed state, as shown in FIG. 12, the pressure element 6' is situated in the receiving part 5' in a position such that the pressure element 6' rests on a head 4 of a bone anchoring element 2, and the deformable portions 601a' 601b' may be positioned slightly below upper wall portions of the through holes 500a', 500b'. Then, crimping tips (not shown) may be introduced into the recesses 600a', 600b' to deform the deformable portions 601a', 601b' towards the outside. The resulting deformed portions 602a', 602b' may abut against the upper wall portion 501a', 501b' of the through holes 500a', 500b' at the inner side of the receiving part 5', as shown in FIG. 13. The deformed portions 602a', 602b' may have a taper of around 45°. When the deformed portions 602a', 602b' abut against the upper wall portions 501a', 501b' of the through holes 500a', 500b', a downward force is exerted onto the head 4 which clamps the head 4 by friction.

The shape of the recesses and blind holes of the embodiments described is not limited to the tapered form. Also the angles of the tapers are not limited to the values described. Other shapes are possible that also achieve a downwardly directed force when the deformable portions are deformed.

For the bone anchoring element, various different kinds of anchoring elements can be used and combined with a receiving part according to embodiments of the invention. These anchoring elements may be, for example, screws with different lengths, screws with different diameters, cannulated screws, screws with different thread forms, nails, hooks, etc. In some embodiments, the head and the shaft can be separate parts which are connectable to each other.

In addition, the shape of the receiving part is not limited to the embodiments shown. For example, the receiving part can have an asymmetric end portion for allowing a greater pivot angle of the bone anchoring element to one side. In some embodiments, the seat for the head may be provided in an insert piece that may be considered part of the receiving part. Also, it is possible to have a recess allowing the rod to be introduced from the side instead of being introduced from the top, or a closed recess through which the rod is guided. Furthermore, various kinds of locking devices, including locking devices having two or more parts, outer nuts, outer caps, bayonet locking devices, or other locking devices may be utilized.

In a further modification, the receiving part may be configured to allow the introduction of the bone anchoring element from the bottom end of the receiving part.

FIGS. 14 to 20b show a further embodiment of a crimping tool that can be used for manufacturing or assembling the polyaxial bone anchoring device. A crimping tool 1000 can be applied to enhance a preload friction force between a pressure element 6 and a head 4 of the bone anchoring element 2 of a pre-assembled bone anchoring device. As can be seen in FIGS. 14 and 15, the crimping tool 1000 is implemented as a hand-held instrument in the form of tongs having a pair of handles 1001, 1001' at one end and a pair of claws 1002, 1002' at an opposite end. Between the handles 1001, 1001' and the claws 1002, 1002', two pairs of levers are arranged. A first pair of levers 1003, 1003' that pivot around a pivot 1003" are connected at one side to the handles 1001. 1001' and at an opposite side to a second pair of levers 1004, 1004' that pivot around a pivot 1004". The pair of levers 1004, 1004' is connected to the pair of levers 1003, 1003' at pivots or hinges 1005, 1005' and is connected at an opposite end to the claws 1002, 1002'. The claws 1002, 1002' are fixed at one end 1002a, 1002a' at respective lever arms of corresponding levers 1004, 1004' that are connected to the lever arms 1003, 1003'. An opposite lever arm of the levers 1004, 1004' are connected via elongate holes 1002b', 1002b to the respective other one of the claws 1002', 1002 (e.g., in a criss-crossing manner). With this construction, the moving of the handles 1001, 1001' together or towards one another causes the claws 1002, 1002' to move towards each other as well, thereby being aligned to be substantially parallel. The crimping tool 1000 may include a spring (not shown) that holds the claws 1002, 1002' in an open position, the spring force of which must be overcome by the handles 1001, 1001 to close the claws 1002, 1002'. The handles 1001, 1001' are shown to be in the same direction as the series of levers 1003, 1003', 1004, 1004' and the claws 1002, 1002'. However, the handles 1001, 1001' may be rotatable at a hinge 1020 so that they are arranged to be perpendicular to the claws 1002, 1002'. This may be of advantage in certain cases or situations. It shall be noted that the crimping tool 1000 can be realized by any other similar construction in which a pressing of handles together causes claws to move towards each other.

As shown in more detail in FIG. 16, the claws 1002, 1002' each have a recess 1006, 1006' that can accommodate a receiving part 5000 of a polyaxial bone anchoring device in a positive-fit manner. At an end of the recess 1006, 1006' in an axial direction along an axis of the crimping tool 1000, a stop 1007, 1007' may be provided against which an upper end portion 5001 of the receiving part 5000 abuts when the receiving part 5000 is inserted into one of the claws 1002, 1002'. The receiving part 5000 may include an asymmetric inclined lower end 5002 for providing a greater pivot angle to one side and an extension 5003 that can be broken off later. This shape is only an example, and the tool may be configured to be utilized with various other receiving parts.

At an inner wall of each recess 1006, 1006', crimping tips 1008, 1008' are provided. The crimping tips 1008, 1008' are located at positions corresponding to central axes A, B of blind-holes 500a, 500b of the receiving part 5000. Hence, when the polyaxial bone anchoring device is inserted and abuts against the stop 1007, the crimping tips 1008, 1008' point in the direction of the central axes A, B of the blind-holes 500a, 500b.

At both sides of each recess 1006, 1006' the claws 1002, 1002' may include teeth 1009, 1009'. The teeth 1009 of one claw 1002 may engage a space between the teeth 1009' of the other claw 1002' when the claws 1002, 1002' move together until they are closed around the receiving part 5000, as shown in FIG. 18.

Operation of the crimping tool 1000 will now be described with reference to FIGS. 16 to 20b. The bone anchoring device 5000 can be delivered, similarly as described before, in a pre-assembled state with the bone anchoring element 2 being inserted and the pressure element 6 being held by crimping in such a way that the U-shaped recess 64 of the pressure element 6 is aligned with the U-shaped recess 56 of the receiving part 5000. By means of the deformed portions 502a, 502b that protrude into the recesses 600a, 600b of the pressure element 6, the pressure element 6 exerts a preload onto the head 4 to frictionally hold the head 4 in a particular angular position.

An additional crimping step can be applied in a case in which the friction force between the pressure element 6 and the head 4 of a pre-assembled polyaxial bone anchoring device is too low. By employing the additional crimping step, the surgeon or any other practitioner or assistant personnel may provide a polyaxial bone anchoring device with a high or greater friction force between the pressure element 6 and the head 4. This can be done at any time before or during surgery. The additional crimping can be carried out, for example, before the bone anchoring element 2 is screwed into a bone or after the bone anchoring element 2 has been screwed into the bone. The crimping tool 1000 may be suitable for performing the crimping after the bone anchoring element 2 has been inserted into the bone. Before surgery, any crimping tool, including the crimping tool 1000, can be used for performing such an additional crimping step.

Figures 19A, 19B:
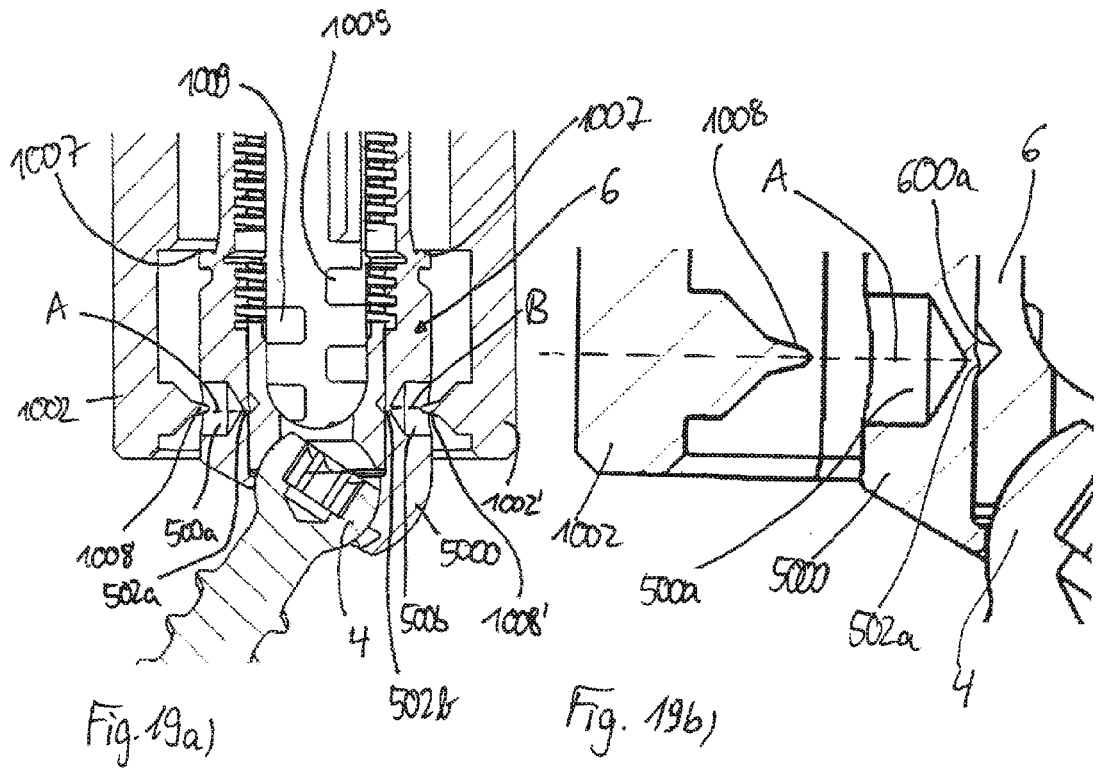

Using the crimping tool 1000, in a first step, the polyaxial bone anchoring device is inserted between the claws 1002, 1002' of the crimping tool 1000, such that the blind-holes 500a, 500b are aligned with the crimping tips 1008, 1008'. Since the stops 1007, 1007' are provided, the crimping tips 1008, 1008' may be automatically located at the correct positions. As shown in FIGS. 19a and 19b, when the claws 1002, 1002' are open, the upper end 5001 of the receiving part 5000 abuts against the stops 1007, 1007' preventing further insertion or advancement of the bone anchoring device into the crimping tool. The central axes of the crimping tips 1008, 1008' are coaxial with the central axes A, B of the blind-holes 500a, 500b, respectively.

Figures 20A, 20B:
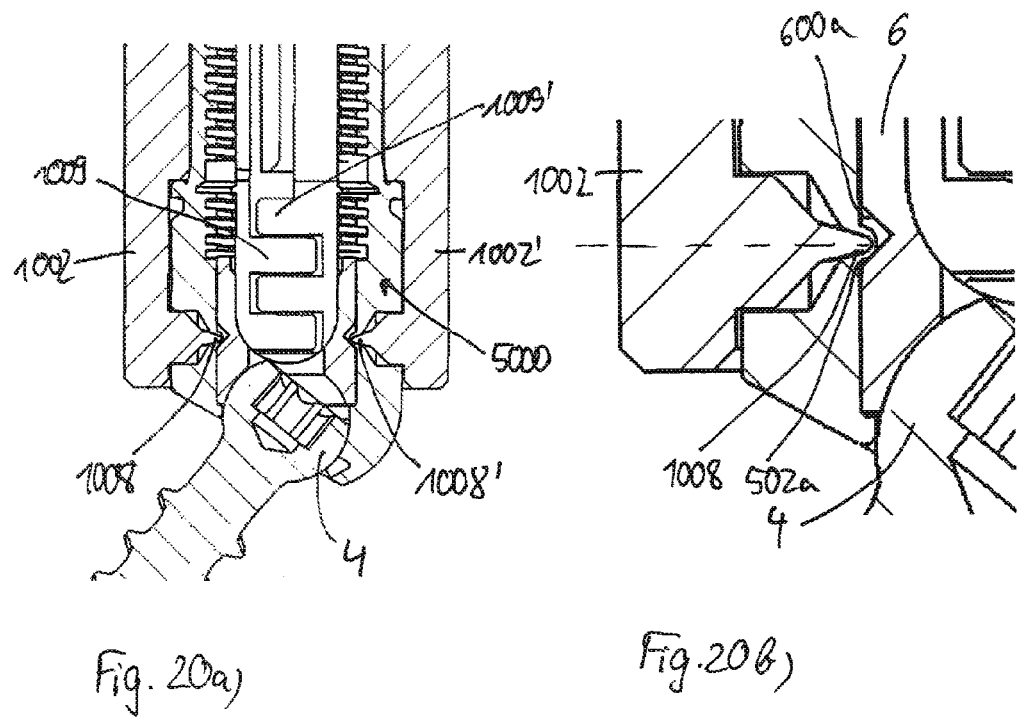

Thereafter, the handles 1001, 1001' are pressed together, thereby closing the claws 1002, 1002', as shown in FIGS. 20a and 20b. The crimping tips 1008, 1008' can be moved towards the direction of the deformed portions 502a, 502b to further deform the deformed portions 502a, 502b so that they extend further into the recesses 600a, 600b of the pressure element 6 and exert a greater downward pressure force onto the pressure element 6. This leads to an increase of the preload force exerted by the pressure element 6 onto the head 4, resulting in a higher friction between the pressure element 6 and the head 4. The movement of the crimping tips 1008, 1008' is limited by the form-fit engagement of the inner contour of the recesses 1006, 1006' with the outer contour of the receiving part 5000. Since this engagement provides a stop, the crimping tips 1008, 1008' move along a path with a defined length to generate a defined deformation of the deformed portions 502a, 502b to enhance the friction force. The claws 1002, 1002' engage each other in a form-fit connection when the teeth 1009' of a lower or first claw 1002' engage the teeth 1009 of an upper or second claw 1002.

Such a crimping tool 1000 can reliably produce a certain high or greater friction force between the pressure element 6 and the head 4.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   an anchoring element having a shaft for anchoring in a bone and a head;
   a receiving part having a first end and a second end, a channel for receiving a rod therein, a bore extending in an axial direction from the first end to the second end, and a seat for receiving the head; and
   a pressure element configured to be arranged in the bore and to exert pressure onto the head when the head and the pressure element are in the receiving part, wherein the head is pivotable and is configured to be locked at an angle relative to the receiving part by the pressure element,
   wherein an outer wall of the pressure element has one of a recess or a deformable portion, and an inner wall of the receiving part has the other one of the deformable portion or the recess, a center of the deformable portion being configured to be between an edge of the recess and a center of the recess when the pressure element is inserted into the receiving part and rests on an inserted head,
   wherein, when the head and the pressure element are in the receiving part, the pressure element is movable from a first position, wherein the deformable portion protrudes a first distance into the recess and engages the recess while the head is pivotable relative to the receiving part, to a second position, wherein the deformable portion protrudes a second distance greater than the first distance into the recess and engages the recess, and
   wherein the pressure element is closer to the second end of the receiving part in the second position than in the first position, such that a force is exerted by the pressure element onto the head to hold the head at one of a plurality of releasable angular positions relative to the receiving part by friction before locking the head in the receiving part.

2. The polyaxial bone anchoring device of claim 1, wherein the deformable portion is configured to plastically deform into a deformed portion.

3. The polyaxial bone anchoring device of claim 1, wherein the recess is at the pressure element and the deformable portion is at the receiving part, and wherein when the pressure element is inserted into the receiving part and rests on the inserted head, the recess has a lower edge having at least a portion that is located closer towards the first end in the axial direction than the center of the deformable portion.

4. The polyaxial bone anchoring device of claim 3, wherein a distance in the axial direction between the lower edge of the recess and the center of the deformable portion is such that a resulting deformed portion of the deformable portion exerts a pressure on the pressure element at the lower edge of the recess to generate a friction force between the head and the pressure element.

5. The polyaxial bone anchoring device of claim 1, wherein the receiving part has a blind hole extending from an outer wall of the receiving part towards the inner wall, and wherein the deformable portion comprises a portion of the receiving part between the inner wall and the blind hole.

6. The polyaxial bone anchoring device of claim 5, wherein a closed end of the blind hole is tapered and forms an angle with a central axis of the bore of less than 45°.

7. The polyaxial bone anchoring device of claim 6, wherein the angle between the closed end of the blind hole and the central axis of the bore is approximately 22.5°.

8. The polyaxial bone anchoring device of claim 1, wherein the recess has an inclined lower edge which forms an angle with a central axis of the bore of approximately 45°.

9. The polyaxial bone anchoring device of claim 1, wherein the deformable portion is deformable to form a tapered protrusion extending from the inner wall of the receiving part into the bore.

10. The polyaxial bone anchoring device of claim 1, wherein when the deformable portion engages the recess to hold the head at the one of the releasable angular positions, the recess provides space for the deformable portion towards the first end in the axial direction.

11. The polyaxial bone anchoring device of claim 1, wherein at least two deformable portions and at least two corresponding recesses are provided, such that two of the at least two deformable portions are respectively offset from one another by 180° in a circumferential direction about the receiving part and two of the at least two recesses are respectively offset from one another by 180° in the circumferential direction.

12. The polyaxial bone anchoring device of claim 1, wherein the deformable portion is at the pressure element and the recess is at the receiving part, and wherein upon deformation of the deformable portion, a resulting deformed portion engages an upper edge of the recess.

13. The polyaxial bone anchoring device of claim 1, wherein the pressure element includes a first end and a second end, a coaxial bore, a spherical recess at the second end, and a cylindrical or U-shaped recess at the first end, and wherein the cylindrical or U-shaped recess is configured to be aligned with the channel of the receiving part when the pressure element is in the receiving part.

14. The polyaxial bone anchoring device of claim 1, wherein the second distance is less than a maximum depth of the recess in a radial direction that is transverse to the axial direction.

15. The polyaxial bone anchoring device of claim 1, wherein the pressure element is a solid member that does not include any spring portions.

16. A method for manufacturing a polyaxial bone anchoring device comprising an anchoring element having a shaft and a head, a receiving part having a first end and a second end, a channel for receiving a rod therein, a bore extending from the first end to the second end in an axial direction, and a seat for pivotably receiving the head, and a pressure element configured to exert pressure onto the head, wherein an outer wall of the pressure element has one of a recess or a deformable portion, and an inner wall of the receiving part has the other one of the deformable portion or the recess the method comprising:
    arranging the pressure element on an inserted head in the receiving part such that a center of the deformable portion is between an edge of the recess and a center of the recess in such a way that the deformable portion can engage the recess upon deformation; and
    deforming the deformable portion to protrude into the recess and to engage the recess, thereby exerting a force onto the pressure element to move the pressure element closer to the second end of the receiving part to a position to hold the head at one of a plurality of releasable angular positions relative to the receiving part by friction, before the pressure element locks the head in the receiving part.

17. The method of claim 16, wherein the recess is at the pressure element and the deformable portion is at the receiving part, and wherein when the pressure element is inserted into the receiving part and rests on the head, the center of the deformable portion is located closer towards the second end in an axial direction than at least a portion of the edge of the recess.

18. The method of claim 16, wherein the recess is at the receiving part and the deformable portion is at the pressure element, and wherein a center of the deformable portion is located closer towards the second end in an axial direction than at least a portion of the edge of the recess.

19. The method of claim 16, wherein the deforming comprises crimping.

20. The method of claim 16, wherein a crimping tool is used to perform the deforming.

21. The method of claim 20, wherein the crimping tool is hand-held.

22. The method of claim 16, wherein the deforming is performed during a pre-assembly step, and wherein a further deformation is made to the deformable portion after the pre-assembly step.

23. A method of coupling a rod to a bone via a polyaxial bone anchoring device, the bone anchoring device comprising an anchoring element having a shaft for anchoring in a bone and a head, a receiving part having a first end and a second end, a channel for receiving a rod therein, a bore extending from the first end to the second end in an axial direction, and a seat for receiving the head, and a pressure element configured to be arranged in the bore and to exert pressure onto the head; wherein an outer wall of the pressure element has one of a recess or a deformable portion, and an inner wall of the receiving part has the other one of the deformable portion or the recess, a center the deformable portion being configured to be between an edge of the recess and a center of the recess when the pressure element is inserted into the receiving part and rests on an inserted head wherein the deformable portion is deformable to protrude into the recess and to engage the recess to move the pressure element to a first position relative to the receiving part where a force is exerted by the pressure element onto the head to hold the head at one of a plurality of releasable angular positions relative to the receiving part by friction, the method comprising:

inserting the bone anchoring device into a bone when the pressure element is in the first position;

applying a force onto the receiving part or the bone anchoring element that is greater than a force of the friction to adjust the angular position between the bone anchoring element and the receiving part;

inserting a rod into the channel; and advancing a locking device into the channel to push the rod against the pressure element and the pressure element against the head to lock the angular position between the bone anchoring element and the receiving part.

24. The method of claim 23, wherein prior to inserting the bone anchoring device into the bone, the method further comprises:

arranging the head of the bone anchoring element in the receiving part;

arranging the pressure element on the head in the receiving part, such that the recess and deformable portion are correspondingly positioned; and deforming the deformable portion to protrude into the recess and to engage the recess, thereby exerting a force onto the pressure element to move the pressure element in the axial direction to the first position.

25. The method of claim 24, wherein a crimping tool is used to deform the deformable portion.

26. The polyaxial bone anchoring device of claim 1, wherein the center of the deformable portion is configured to be closer to the edge of the recess than the center of the recess when the pressure element is inserted into the receiving part and rests on an inserted head.

\* \* \* \* \*